US005789570A

United States Patent [19]

Buchholz et al.

[11] Patent Number: 5,789,570
[45] Date of Patent: Aug. 4, 1998

[54] SWELLABLE STARCH ESTER AND METHODS OF ITS PRODUCTION AND USE

[75] Inventors: Stefan Buchholz; Klaus Dorn, both of Hanau; Thomas Eurich, Frankfurt, all of Germany

[73] Assignee: Degussa Aktiengesellschaft, Frankfurt, Germany

[21] Appl. No.: 563,405

[22] Filed: Nov. 30, 1995

[30] Foreign Application Priority Data

Nov. 30, 1994 [DE] Germany .................. 44 42 606.2

[51] Int. Cl.[6] .................. C08B 31/04; C09K 3/32; C09K 17/32
[52] U.S. Cl. .................. 536/107; 536/110; 536/123
[58] Field of Search .................. 536/107, 110, 536/123; 502/404; 524/35; 604/338, 365; 206/802; 523/100; 106/805; 504/162, 164; 47/48.5, 59

[56] References Cited

U.S. PATENT DOCUMENTS 2,461,139  2/1949  Caldwell .
4,002,173  1/1977  Manning et al. .................. 128/296
4,129,722  12/1978  Iovine et al. .................. 536/43

FOREIGN PATENT DOCUMENTS 25 33 005   2/1976   German Dem. Rep. .
56-152806   11/1981  Japan .
63035644    11/1981  Japan .
56-155203   12/1981  Japan .
631 085      7/1982  Switzerland .

OTHER PUBLICATIONS

JP-A-56 155 203, "Carboxyl Contain Polymer Preparation React Carboxylic Acid Anhydride Hydroxyl Contain Polymer Presence Water Absence Water", *Derwent Publications Ltd.*, Dec. 1981.

*Primary Examiner*—Nathan M. Nutter
*Attorney, Agent, or Firm*—Cushman Darby&Cushman IP Group of Pillsbury Madison & Sutro LLP

[57] ABSTRACT

A biodegradable, swellable starch ester, containing more than 50% by weight of water-insoluble components and having a retention capacity of >500% for 0.9% (by weight) aqueous NaCl solution, and methods of its production and use.

4 Claims, No Drawings

SWELLABLE STARCH ESTER AND METHODS OF ITS PRODUCTION AND USE

BACKGROUND OF THE INVENTION

1. Field of the Invention

The invention relates to absorption material which is based primarily on renewable raw materials and exhibits a biological degradability which is distinctly better than that of the polyacrylates currently primarily used as absorber material.

The invention relates in particular to a swellable starch ester which exhibits a comparatively high absorption capacity and which displays only a slight tendency toward gel blocking in comparison to other absorber materials based on polysaccharide. Moreover, the invention discloses methods of producing the absorption material in accordance with the invention as well as the use of the products.

2. Background Information

By far most of the absorption materials used today, frequently also designated as superabsorbers, consist of weakly cross-linked polyacrylates and are therefore poorly degradable or nondegradable (see e.g. Stegman et al., Waste Manage. Res. 11 (1993) 155).

In addition to the pure polyacrylates there are also polyacrylates grafted onto starch (DE-A 26 12 846). However, the starch content of these products is low (25% or less). In the case of higher starch contents a distinct deterioration of the absorption qualities is observed. Due to the polyacrylate content the biological degradability (biodegradability) of these products is also low.

Likewise, up to approximately 25% of a polysaccharide which is water-soluble at least to a limited degree can be worked into a cross-linked polyacrylate superabsorber by bringing the polysaccharide into the reaction mixture during the polymerization of the acrylate (DE-A 40 29 591, DE-A 40 29 592, DE-A 40 29 593).

U.S. Pat. No. 5,079,354 describes an absorber material based on carboxymethyl starch, that is, a starch ether, produced by reacting starch with chloroacetic acid. In this process an equivalent amount of sodium chloride relative to the chloroacetic used is released, which is undesirable for ecological reasons. It is also known that etherified polysaccharides with high degrees of substitution are only poorly biodegradable (Mehltretter et al., J. Am. Oil Chem. Soc. 47 (1970) 522).

DE-A 31 32 976 teaches the use of starch succinate derivatives as extenders for dry, solid absorption agents swellable in water based on an ionically complexed, anionic polyelectrolyte, e.g. a polyacrylic acid/aluminum cation complex. DE-A 31 32 976 lists a whole series of potential extenders which also improve the absorption qualities of the mixtures containing them with, for example, polyacrylic acid. Thus, extenders which are to be mixed preferably with rather strongly surface-treated, ionically complexed polyelectrolytes include in particular sodium carboxymethylcellulose, methylcellulose, finely dispersed attapulgite clay, mixtures of sodium carboxymethylcellulose with attapulgite clay or with coarse or fine montmorillonite clay, cold-water-dispersable waxy corn starch and starch succinate derivatives. In examples, mixtures of 40% roller-dried starch succinate derivative and 60% polyelectrolyte show only a slight improvement of the blood-salt-pressure retention of the pure polyelectrolyte without extender. For a pure, roller-dried starch succinate derivative, a value of 4.0 g/g is indicated for comparison purposes as result of the blood-salt-pressure retention test. This value is approximately ⅕ of the pure polyelectrolyte.

EP-A 0,603,837 describes the production of starch esters using organic acid anhydrides. To this end, starch of various origins is reacted in a one-stage, aqueous method with organic acid anhydrides of general formula I:

in which R signifies alkyl, aryl, alkenyl, alkaryl or aralkyl with 1 to 7C atoms under certain conditions of pH, temperature and concentration. Exemplary starch esters listed in the specification of EP-A 0,603,837 include starch acetate, starch propionate, starch butyrate, starch hexanoate, starch benzoate or also mixed starch acetates/propionates. The use of propionic acid anhydride, acetane hydride and/or butyric acid anhydride is disclosed in the examples of EP-A 0,603,837. The method described in EP-A 0,603,837 makes it possible to avoid the problems which otherwise resulted when rather large amounts of anhydride were used such as, for example, the swelling or gelatinizing of the starch and problems during the separation of the starch esters from the reaction mixture. The product becomes hydrophobic by the reaction and can therefore be filtered off in a simple manner.

WO 93/01217 (PCT/EP 92/01553) teaches a method of producing starch esters for clinical, especially parenteral use. In order to produce water-soluble, physiologically compatible starch esters, starch is converted by acid hydrolysis or enzyme hydrolysis into a partial hydrolysate with an average $M_W$ in a range of 10.000 to 500.000 daltons, this partial hydrolysate acylated in aqueous solution with the anhydride or halide of an aliphatic monocarboxylic acid with 2–4 carbon atoms or of an aliphatic dicarboxylic acid with 3–6 carbon atoms or mixtures thereof and with an alkalizing agent up to a molar substitution in a range of 0.1 to 1.0 mole/mole.

The starch esters according to WO 93/01217 are quite water-soluble, which is required for parenteral use.

An acetyl starch obtainable by reacting a waxy corn starch partial hydrolysate with acetic acid anhydride can be gathered, for example, from the examples of this application as blood-plasma thickener.

Although further starches and anhydrides are cited in WO 93/01217, for example, anhydrides or halides of a dicarboxylic acid, e.g. succinic acid or maleic acid, this publication teaches exclusively the production of water-soluble, physiologically compatible starch esters.

There have also been attempts to create biologically degradable superabsorbers. Thus, DE-A 42 06 857 teaches an absorption agent consisting of a component based on special, renewable polysaccharide raw materials, of a special, water-swellable polymer, of a matrix material, of an ionic or covalent cross-linking agent and of a reactive additive. The component based on renewable polysaccharide raw materials comprises e.g. guar, carboxymethylguar, xanthan gum, alginates, gum arabic, hydroxyethyl- or hydroxypropylcellulose, carboxymethylcellulose and other cellulose derivatives, starch and starch derivatives such as carboxymethyl starch. DE-A 42 06 857 also teaches that the cited polymers can be modified by cross-linking in order to reduce their solubility in water and to achieve better swelling qualities. The cross-linking can take place either in the entire polymer or only on the surface of the individual polymer particles.

The reaction of the polymers can take place with ionic cross-linking agents such as e.g. alcium-, aluminum-, zirconium- and iron(III)-compounds. Also possible is a reaction with multifunctional carboxylic acids such as citric acid, mucic acid, tartaric acid, malic acid, malonic acid, succinic acid, glutaric acid, adipic acid, with alcohols such as polyethylene glycols, glycerol, pentaerythrite, propane diols, saccharose, with epoxides such as glycol diglycidylether, glycol di- or -triglycidylether and epichlorohydrin, with acid anhydrides such as succinic acid anhydride and maleic acid anhydride, with aldehydes and multifunctional (activated) olefines such as bis-(acrylamido) acetic acid and methylene bisacrylamide. Naturally, derivatives of the named classes of compounds can also be considered as well as heterofunctional compounds with different functional groups of the above-named classes of compounds.

Although the systems presented and documented in examples and based on sodium carboxymethylcellulose in conjunction with sodium polyacrylate exhibit quite favorable absorption qualities in various tests, the publication does not disclose more detailed information about the biological degradability with the exception of the fact that the latter is simply asserted.

However, it is known that polyacrylates are practically not biologically degradable at all (R. Stegmann et al., Waste Water Res. 11(2) (1993), p. 155) and carboxymethylcellulose, a polysaccharide ether, is only very poorly biologically degradable (4.6% after 5 days; M. Seekamp, Textilveredlung 25 (1990), p. 125).

SUMMARY OF THE INVENTION

In view of the state of the art, the objective of the invention was to develop an absorption material with a biological degradability which is superior to that of the polyacrylates currently primarily used, as well as making available a simple method of its production.

This problem and others which are not cited in detail are solved by a swellable starch ester which consists of more than 50% by weight of water-insoluble components, and has a retention capacity for 0.9% by weight aqueous NaCl solution of >500% relative in each instance to the weight of the dry starch ester, which retention capacity is determined by allowing 0.1 g of the starch ester welded into a nylon bag with a mesh width of 52 μm to swell for 30 min. in a 0.9% NaCl solution, centrifuging the bag subsequently for 5 min. at 1400 rpms and then gravimetrically determining any resulting weight increase.

It was surprisingly found in the development of the invention that a product which is very swellable but more than 50% insoluble can be obtained during the modification of starch which is soluble in cold water, that is, pre-gelatinized. This material is suitable for use as absorption material for absorbing water, aqueous solutions, dispersions and body fluids in hygiene and animal hygiene, especially in diapers and incontinence products. It can also be used in packaging materials for meat and fish as well as for soil improvement, including use in pots [i.e. agricultural culturing pots], and as cable jacketings. At the same time, it has excellent biodegradability.

In contrast to the substances indicated in DE-A 42 06 857 as component A, whose biological degradability is simply asserted because they are based, as is stated, on special, renewable polysaccharide raw materials, the superabsorber materials in accordance with the present invention are actually biologically degradable, as will be explained later in more detail using model compounds.

In a preferred embodiment of the invention the starch ester is characterized by a retention capacity of >1500% for 0.9% by weight aqueous NaCl solution, relative to the weight of the dry, non-swollen starch ester.

The starch esters in accordance with the invention are products with a degree of substitution between 0.2 and 2.0; the degree of substitution indicates the number of substituents per glucose ring. The esters can be products with only one type of ester group or with mixed esters.

The esters are preferably obtained by reacting starch with acid anhydrides, which anhydrides can be cyclic and/or open-chain anhydrides. According to the invention maleic acid anhydride is preferred.

Principally non-ionic starch esters result from the reaction of starch with open-chain anhydrides whereas the reaction of starch with cyclic anhydrides results in basically ionic starch esters carrying carboxylate groups. In order to obtain the absorption materials of the invention, which are swellable but more than 50% insoluble, it is particularly preferable if the product contains free carboxyl- and/or carboxylate groups. It is therefore advantageous if at least a part of the anhydride used is a cyclic anhydride.

Furthermore, a product is preferred which carries double bonds at least in a part of the side groups. The maleic acid ester of the starch embodies these two desired properties in a quite especially preferred manner.

When reacting cold-water-soluble (pre-gelatinized) starch with, for example, succinic acid anhydride, a water-soluble product is obtained. The probable cause for the insolubility of the maleic acid product is therefore cross-linking which takes place via a Michael reaction on the double bond of the maleic acid side group.

DE-A 42 06 857 describes, as mentioned above, an absorption agent which can contain a starch or a starch derivative in addition to the non-biodegradable polyacrylate. In this connection DE-A 42 06 857 describes the cross-linking of starch or starch derivatives such as carboxymethyl starch (that is, a starch ether) with maleic acid anhydride for lowering the solubility along with as associated improvement of the swelling qualities. In contrast thereto, the present invention is based on the recognition that ionic groups can be introduced into the polysaccharide skeleton without the use of biologically non-degradable polyacrylate, by the esterification of starch or starch derivatives with carboxylic acid anhydrides and especially with maleic acid anhydride according to the equation

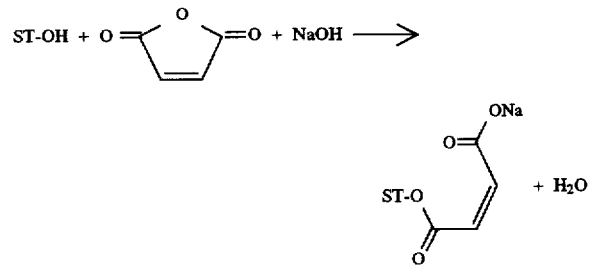

in which ST-OH stands for starch or a starch derivative. The presence of these ionic groups results in especially favorable absorption and swelling qualities because of the osmotic pressure caused by them and thereby results in excellent biological degradability.

In order to achieve an advantageous swelling capacity, cross-linking is necessary in addition to the introduction of these ionic groups, in order to convert the material into a form which can swell, but is insoluble in water.

Both the esterification which introduces the ionic groups and cross-linking take place within the framework of the invention in an especially advantageous manner, with maleic acid anhydride or a mixture of at least two anhydrides of which one is maleic acid anhydride, preferably in a single step. However, if the molecule lacks a sufficient number of ionic groups, as is the case according to DE-A 42 06 857, a totally different product results which does not have the swelling capacity in conjunction with the retention capacity of the swellable starch esters of the invention. Carboxylic acid anhydrides which can be used in an especially advantageous manner together with maleic acid anhydride include, among others, acetic anhydride, propionic acid anhydride and/or succinic acid anhydride.

In principle, any native, modified or substituted starch can be used as the starch base of the materials of the invention. Such starches can be isolated from any vegetable source and comprise, for example, potato starch, corn starch, wheat starch, waxy corn starch and starches with a high amylose content. Starch meal can also be used. Modified products based on one of the above-mentioned starches can also be used such as e.g. acid-hydrolysed starch, enzyme-hydrolysed starch, dextrines and oxidized starch. Moreover, derivatized starches such as cationic starch, anionic starch, amphoteric starch or non-ionically modified starch such as e.g. hydroxyethyl starch can be used. The starches used can be granular or pre-gelatinized starch and the destruction of the granular structure can take place thermally, mechanically or chemically.

The use of cold-water-soluble starch is especially advantageous for the invention. This includes in particular pre-gelatinized or partially degraded starch. See in this connection, among others, Aeromyl 115 of the Südstärke company.

The invention is also provides a method of producing a starch ester in which starch or modified starch is reacted in a one-stage aqueous reaction with a carboxylic acid anhydride or a mixture of carboxylic acid anhydrides at a pH of 7 to 11 and a temperature of 0° to 40° C., which pH is maintained in the desired range by adding aqueous alkali solution with a concentration of approximately 10 to 50%. The production method is also characterized in that a cyclic, unsaturated anhydride or a mixture of carboxylic acid anhydrides comprising such a cyclic, unsaturated anhydride is used as carboxylic acid anhydride.

The pH is preferably maintained constant during the reaction of the anhydride with the starch. The pH should be between 7 and 11 during the reaction. A pH between 8 and 9 is preferred. The pH can in principle be maintained constant by adding any desired alkaline material. Alkali- and alkaline-earth hydroxides as well as the oxides and carbonates of these metals are especially useful. Sodium hydroxide, potassium hydroxide, calcium hydroxide, ammonium hydroxide, magnesium hydroxide and sodium carbonate are cited by way of example. When producing products with a relatively high degree of substitution it is preferable to use an alkali solution with a relatively high concentration, approximately 10 to 50%, in order to avoid an unnecessary dilution of the reaction medium.

The invention also includes a method of producing a starch ester in which starch or modified starch is reacted with a carboxylic acid anhydride or a mixture of carboxylic acid anhydrides in the presence of a base and, if necessary, of a solvent. The method is characterized in that the mixture is allowed to react for 10 min. to 10 h at a temperature of 80° to 180° C. and that solvent is tolerated only up to a content of less than 100 parts relative to 100 parts starch.[1]

[1]Sodium carbonate is preferably used as above in the above-mentioned method. Still, it is especially advantageous to use maleic acid anhydride as carboxylic acid anhydride or a mixture of anhydrides of which one is maleic acid anhydride.

The invention also includes the use of starch ester in an amount of 100 parts by weight together with 0.7–70 parts by weight of an antiblocking agent based on natural or synthetic, preferably hydrophilic fibers or materials with a large surface as superabsorber. The use of starch ester as superabsorber together with 1 to 5 parts by weight silicic acid or cellulose fibers as antiblocking agent is preferred.

The starch ester of the invention is further used as absorption material for absorbing water, aqueous solutions, dispersions and body fluids in hygiene and animal hygiene, especially in diapers, tampons and incontinence products as well as in packaging materials for meat and fish, as absorption material for absorbing water and aqueous solutions in agricultural pots and for soil improvement or as absorption material for absorbing water and aqueous solutions in cable jacketings.

DETAILED DESCRIPTION OF THE INVENTION

The materials of the invention are at least partially biodegradable. There is currently still no generally recognized test for determining the biological degradability for swellable but water-insoluble products. Nevertheless, in order to be able to make an at least qualitative statement a dextrine maleate with a DS (th.)=1 and DS(NaOH)=0.92 was investigated regarding its biological degradability as water-soluble, oligomeric model compound. The model compound was 65% degraded in the Zahn-Wellens test within 28 days and 95% degraded within 42 days. Even a dextrine maleate with a very high degree of substitution, DS (th.)=2.0 and DS(NaOH)=1.47 was 66% degraded within 28 days in the Zahn-Wellens test and 88% degraded within 42 days.

A cross-linked product analogous to example 1, a starch maleate with a DS(th.)=1.0 and DS(NaOH)=0.81 was 30% degraded within 28 days and the biological degradation rose even further after 28 days. The slight degradation of the cross-linked product is probably traceable to the relatively poor accessibility of the polymers in the cross-linked product since in the latter the microorganisms and enzymes can attack the gel particles only from the surface. However, since an approximately linear increase of the biological degradation in time is observed even after 28 days, it seems reasonable to assume that the products of the invention and especially starch maleate can in principle be completely degraded biologically. This assumption is further supported by the fact that starch succinate, another anionic starch ester which is, however, water-soluble, is 90% biologically degraded within 28 days.

By way of comparison: On the other hand, a biological degradation of only 13% after 21 days is found for carboxymethyl starch, a starch ether with a theoretical DS of 1.0, which documents the poor biological degradability of starch ethers known in the literature (Mehltretter et al., J. Am. Oil Chem. Soc. 47 (1970) 522).

Determination of the substitution yield via the NaOH consumption during synthesis During the reaction of starch with maleic acid anhydride (MSA) [German abbrev.] in aqueous solution one mole NaOH is consumed per mole maleic acid anhydride. If no addition of the maleic acid anhydride to the starch takes place but rather a hydrolysis to disodium maleate then 2 moles NaOH are consumed per mole MSA with the pH being maintained constant. If no more non-reacted anhydride is present at the end of the reaction the degree of substitution can be calculated according to $$DS = 1 - \frac{\text{(consumption of NaOH in moles} - \text{amount of } MSA \text{ used in moles)}}{\text{(amount of } MSA \text{ used in moles)}}$$

The degree of substitution determined in this manner is designated in the following with DS(NaOH).

Method of determining the retention capacity

A tea-bag test was performed to determine the retention capacity. For this, 0.10 g of the test substance is weighed into a bag of nylon tissue with a mesh width of 52 μm. The welded nylon bag is placed into a 0.9% NaCl solution and the test material is allowed to swell for 30 minutes. The bag is then removed and centrifuged 5 minutes at 1400 rpms in a centrifuge tray with perforated bottom. The absorption of liquid is gravimetrically determined and converted to 1 g of the substance to be tested. The value obtained in this manner is designated as retention capacity (abbreviated SRV for "saline retention value").

Method of determining the absorption capacity with and without load 0.5 g of the test substance is placed on a G3 glass frit with a diameter of 3 cm. The frit is connected to a burette by a hose, which burette is filled with 0.9% NaCl solution. The amount of liquid is determined which the test substance absorbs in 10 minutes. During the test time the burette is refilled in such a manner that the meniscus is always at the level of the glass frit. The value determined in this manner is converted to 1 g test substance and designated with A(NaCl).

In another embodiment a weight exerting a pressure of 20 g/cm$^2$ is placed on the test substance. The value obtained in this manner is also converted to 1 g test substance and abbreviated with AUL(NaCl) (absorption under load).

Determination of the soluble components

In order to determine the soluble components 1 g of the product to be characterized is placed in 100 ml demineralized water and the mixture agitated 24 hours at room temperature. The gel particles produced are centrifuged off and a specimen of approximately 10 ml removed from the supernatant solution, weighed, evaporated to dryness; the residue is weighed, and from the measured amount the soluble portion of the absorber material is calculated.

Biological degradation according to Zahn-Wellens

The degradation test according to Zahn and Wellens is an aid for evaluating the biological degradability of a substance or of a waste water. It can be used quantitatively only for water-soluble substances. For substances which are not completely soluble it offers only a qualitative indication of whether these substances are basically susceptable to biological degradation or not.

Approximately 2 l biomass suspension are agitated in a tall, 3 l beaker and aerated over glass frits. 385 mg NH$_4$Cl and 89 mg NaH$_2$PO$_4$.H$_2$O are weighed in, compounded with the calculated polymer amount and filled with cold tap water to approximately 2 l. The active sludge from a municipal sewage treatment plant is allowed to settle 30–60 min. so that it is reduced in volume by one half. The supernatant water is decanted off and the sludge preserved under agitation and aeration. A part of the sludge is taken therefrom and centrifuged 5 min. at 200 rpms. 24 g of the centrifuged sludge on a 2 l batch yield a dry substance content of 1 g/l (±200%). Before the addition of the sludge to the polymer solution the pH is adjusted to 6.5–7.0 and a specimen analyzed for its COD (chemical oxygen demand) content. After the active sludge is finely distributed another specimen can be taken. The height of the liquid in the beaker is then marked. For comparison, a test is prepared containing only nutrient salts and active sludge but no polymer. This batch serves to determine the COD caused by the activated sludge. The biosludge deposited on the edge of the beaker is wiped back into the solution daily with a rubber wiper, the pH readjusted and evaporated water replaced by demineralized water. In order to determine the substance absorbed on the biosludge two specimens are analyzed for their COD, a non-filtered specimen is removed directly from the well-mixed reaction vessel and measured. An aliquot part, e.g. 40 ml, is removed for the specimen to be filtered, allowed to settle and filtered via a Millipor 2.5μ filter (e.g. Millipor Millex GS). The clear solution is also analyzed for its COD.

Calculation

In order to determine the COD content of the substance adsorbed on the biomass the COD value of the filtered specimen and the blank reading with biomass are subtracted from the COD in the specimen solution.

| P1 | non-filtered specimen solution with sludge |
|---|---|
| P2 | filtered specimen solution |
| Bld | non-filtered blank reading |
| ad | adsorbed substance |
| P1-P2-Bld = ad | |

If the filtered blank reading is subtracted from filtered specimen P2 the dissolved substance is obtained.

| B1 | filtered blank reading |
|---|---|
| S | dissolved substance |
| P2-Bi = S | |

The adsorbed and the dissolved substances together yield the initial content of matter to be degraded and the content at the time. The biological degradation η is calculated as A    initial value
η    biological degradation $$\eta = \frac{A - (ad + s)}{A} \cdot 100$$

EXAMPLES

Example 1

Synthesis of Starch Maleate 50 g (=0.276 mole) Aeromyl 115 (physically modified, cold-water-soluble starch of the Südstärke company; residual moisture=ca. 12%) are dissolved in 400 ml water. The pH is adjusted with 3N NaOH to 8 and maintained constant during the reaction. 27.1 g (=0.276 mole) solid maleic acid anhydride are added at a reaction temperature of 0° C. over a period of 2 h. The mixture is agitated for 3 more h at 25° C. (post-reaction). The degree of substitution (DS(NaOH)) is 0.81.

The reaction solution is evaporated to dryness and dried in a vacuum drying oven.

SRV=19.1 g/g; A(NaCl)=13.2 ml/g

Example 2

Synthesis of Starch Maleate

Like example 1, but the reaction solution is freeze-dried.

SRV=16.3; A(NaCl)=14.8 ml/g; soluble components=35.2%

Example 3

The product of example 2 is mixed with 5% of a precipitation silicic acid (FK 500 LS, Degussa AG).

A(NaCl)=21.2 ml/g, AUL(NaCl)=5.4 ml/g

Example 4

Synthesis of Starch Maleate 50 g (=0.269 mole) Aeromyl 115 (physically modified, cold-water-soluble starch of the Süadstärke company; residual moisture=ca. 12%) are dissolved in 400 ml water. The pH is adjusted with 3N NaOH to 8 and maintained constant during the reaction. 13.2 g (0.135 mole) solid maleic acid anhydride are added at a reaction temperature of 0° C. over a period of 2 hours. The mixture is agitated 3 h further at 25° C. (post-reaction). The substitution yield is 83.1% and the degree of substitution is correspondingly 0.42.

The reaction solution is precipitated by pouring the reaction solution into acetone and dried in a vacuum drying oven at temperatures <50° C.

SRV=11.0 g/g; A(NaCl)=14.9 ml/g, AUL(NaCl)=7.6 ml/g

Example 5

Solid-Phase Synthesis of Starch Maleate 100 parts Aeromyl 115 (physically modified, cold-water-soluble starch of the S-adstarke company; residual moisture=approximately 12%) are mixed with 60 parts maleic acid anhydride and 65 parts sodium carbonate. The mixture is tempered 3 hours at 80° C. in a fixed bed.

SRV=6.6 ml/g

Example 6

Synthesis of a Mixed Starch Ester 50 g (=0.276 mole) Aeromyl 115 (physically modified, cold-water-soluble starch of the Südstärke company; residual moisture =ca. 12%) are dissolved in 400 ml water. The pH is adjusted with 3N NaOH to 8 and maintained constant during the reaction. A mixture of 13.36 g (=0.136 mole) solid maleic acid anhydride and 13.61 g (0.136 mole) solid succinic acid anhydride is added at a reaction temperature of 0° C. over a period of 2 h. The mixture is agitated for 3 more h at 25° C. (post-reaction). The degree of substitution (DS(NaOH)) is 0.80.

The reaction solution is evaporated to dryness and dried in a vacuum drying oven.

SRV=15.5 g/g; A(NaCl)=4.6 ml/g

Example 7

The product of example 2 is mixed with 5% of a precipitation silicic acid (FK500LS, Degussa AG).

A(NaCl)=24.8 ml/g; AUL(NaCl)=3.8 ml/g

Reference Example 1

Synthesis of Starch Succinate 50 g (=0.278 mole) Aeromyl 115 (physically modified, cold-water-soluble starch of the Südstarke company; residual moisture=11.9%) are dissolved in 400 ml water. The pH is adjusted with 3N NaOH to 9 and maintained constant during the reaction. 31.5 g (=0.315 mole) solid succinic acid anhydride is added at a reaction temperature of 25° C. over a period of 2 h. The mixture is agitated for 3 h more at 25° C. and the product subsequently precipitated by the addition of acetone. The product is filtered off and dried at RT in a vacuum drying oven. The substitution yield is 81% and the degree of substitution 0.92.

SRV—Can not be determined since the product flows out of the nylon sieve bag on account of its water solubility.

Further embodiments and advantages of the invention result from the following patent claims. References cited herein are hereby incorporated by reference.

What is claimed is:

1. A method of producing a starch ester consisting of more than 50% by weight of water-insoluble components and having a retention capacity of >500% for 0.9% (by weight) aqueous NaCl solution, relative in each instance to the weight of the dry starch ester, said retention capacity being determined by allowing 0.1 g of the starch ester welded into a nylon bag with a mesh width of 52 μm to swell for 30 min. in a 0.9% NaCl solution, centrifuging the bag for 5 min. at 1400 rpm, and gravimetrically determining any weight increase, said method comprising reacting starch or modified starch in a one-stage aqueous reaction with maleic anhydride or a mixture of carboxylic acid anhydrides containing maleic anhydride at a pH of 7 to 11 and a temperature of 0° to 40° C.; and maintaining the pH in the desired range by adding aqueous alkali solution with a concentration of approximately 10 to 50%.

2. A method of producing a starch ester consisting of more than 50% by weight of water-insoluble components and having a retention capacity of >500% for 0.9% (by weight) aqueous NaCl solution, relative in each instance to the weight of the dry starch ester, said retention capacity being determined by allowing 0.1 g of the starch ester welded into a nylon bag with a mesh width of 52 μm to swell for 30 min. in a 0.9% NaCl solution, centrifuging the bag for 5 min. at 1400 rpm, and gravimetrically determining any weight increase, said method comprising reacting starch or modified starch in a reaction mixture with a carboxylic acid anhydride or a mixture of carboxylic acid anhydrides in the presence of a base at a temperature of 80° to 180° C. for 10 min. to 10 h.

3. The method according to claim 2, further comprising adding up to about 100 parts of a solvent relative to 100 parts starch to said reaction mixture.

4. The method according to claim 2, characterized in that said base comprises sodium carbonate.

* * * * *